United States Patent [19]

Ogawa et al.

[11] Patent Number: 5,571,622

[45] Date of Patent: Nov. 5, 1996

[54] WATER- AND OIL REPELLENT SUBSTRATE AND METHOD OF TREATMENT

[75] Inventors: Kazufumi Ogawa, Nara; Mamoru Soga, Osaka, both of Japan

[73] Assignee: Matsushita Electric Industrial Co., Ltd., Osaka, Japan

[21] Appl. No.: 309,545

[22] Filed: Sep. 20, 1994

Related U.S. Application Data

[63] Continuation of Ser. No. 914,533, Jul. 17, 1992, abandoned.

[30] Foreign Application Priority Data

Jul. 26, 1991 [JP] Japan .................................. 3-187693
Jul. 26, 1991 [JP] Japan .................................. 3-187695

[51] Int. Cl.$^6$ .................................................. B32B 9/00
[52] U.S. Cl. ........................ 428/391; 428/375; 428/447; 428/913; 428/367
[58] Field of Search ............................ 428/391, 375, 428/447, 367, 913

[56] References Cited

U.S. PATENT DOCUMENTS

| | | | |
|---|---|---|---|
| Re. 25,622 | 7/1964 | MacMullen | 428/391 |
| 2,531,571 | 11/1950 | Hyde | 428/391 |
| 2,563,288 | 8/1951 | Steinman | 428/391 |
| 3,859,320 | 1/1975 | Atherton | 428/391 |
| 4,539,061 | 9/1985 | Sagiv | 156/278 |
| 4,761,316 | 8/1988 | Ogawa | 428/64 |
| 5,011,963 | 4/1991 | Ogawa et al. | 556/485 |
| 5,124,374 | 6/1992 | Baker et al. | 428/391 |
| 5,130,194 | 7/1992 | Baker et al. | 428/391 |
| 5,209,976 | 5/1972 | Ogawa et al. | 428/391 |
| 5,378,521 | 1/1995 | Ogawa et al. | 428/85 |

FOREIGN PATENT DOCUMENTS

| | | |
|---|---|---|
| 0482613 | 4/1992 | European Pat. Off. |
| 0484886 | 5/1992 | European Pat. Off. |
| 0491251 | 6/1992 | European Pat. Off. |
| 0493747 | 7/1992 | European Pat. Off. |
| 0497189 | 8/1992 | European Pat. Off. |
| 0508136 | 10/1992 | European Pat. Off. |

*Primary Examiner*—N. Edwards
*Assistant Examiner*—J. M. Gray
*Attorney, Agent, or Firm*—Fish & Richardson P.C.

[57] ABSTRACT

A durable and extremely water- and oil repellent ultra thin film is formed on the surface of a substates such as glass, ceramics, fabrics, fur and cloth by a dehydrochlorination reaction between a functional group such as a hydroxyl group or an imino group on the surface of the substrate. The coating film of the material comprises a plurality of chlorosilyl groups was formed on the surface of the substrate by dipping and holding the substrate comprising functional groups on its surface in a solution prepared by dissolving a material comprising fluorocarbon groups and a plurality of chlorosily groups in a non-aqueous solvent and drying the substrate which is then taken out from the solution in a substantially moistureless or low moisture atmosphere and removing the non-aqueous solvent remaining on the substrate. Further, when the coating film is left in an atmosphere comprising moisture, i.e., humid air, the coating film is polymerized by a dehydrochlorination reaction between the coating film and the moisture in the atmosphere. The film is formed on the surface of the substrate containing hydroxyl groups, imino groups or carboxyl groups through —SiO— bonds or —SiN< bonds.

1 Claim, 2 Drawing Sheets

WATER- AND OIL REPELLENT SUBSTRATE AND METHOD OF TREATMENT

This application is a continuation of U.S. application Ser. No. 07/914,533, filed Jul. 17, 1992, now abandoned.

FIELD OF THE PRESENT INVENTION

This invention relates to a method of making the surface of a substrate water- and oil repellent. More particularly, this invention relates to a method of making the surface of substrates, such as metal, ceramics, glass, plastic, fiber and paper, water- and oil repellent by forming a water- and oil repellent ultra thin film on the surface of the substrates.

Further, this invention relates to water- and oil repellent materials for apparel. Particularly, this invention relates to an efficient water- and oil repellent and antifouling materials for apparel such as rainwear, coats, sportwear (for example ski wear), cloth for gloves, fur and leather.

BACKGROUND OF THE INVENTION

In the prior art, the surface of the materials such as metal, ceramics, glass, plastic, fiber, paper and wood were made water- and oil repellent by impregnating or coating resins and paints or by applying or baking an emulsion of a fluorocarbon resin such as polytetrafluoroethylene. In addition, making rainwear, coats, sportwear (including ski wear), cloth for gloves, fur and leather water- and oil repellent is an important object for antifouling materials for apparel and for rainy weather measures.

In the prior art, a method of spraying a fluorocarbon based emulsion (fluorocarbon resin) and forming a loose coating film having minute holes was proposed to make materials for apparel such as textiles with keeping air permeability to some extent. Another method of coating resins such as with a thin urethane resin to form a loose coating film having minute holes was proposed. Another method of densely weaving thin fiber having a relatively high shrinkage percentage and shrinking the textiles by a high temperature processing is also known. Further, a natural fur such as mink is polish processed by applying materials comprising a silicon compound or a fluorine compound.

However, in the prior art, the coated film was not chemically bonded to the surface of the substrate, thus it was a serious drawback that the durablity of the coated film was extremely poor. In addition, there was a problem that the appearance of the substrate was damaged by the prior art methods. In addition, the prior method of coating water repellent materials had only a minor effect on the substrate, thus the durability of the coating was extremely poor. The body also gets sweaty when wearing clothes whose surface was coated with resin. It is an extremely important improvement in material for apparel that only the surface fiber is made water repellent without damaging the luster of the fiber and the comfortable feeling of texitiles and air permeability of the fiber is maintained.

SUMMARY OF THE INVENTION

It is a primary object of this invention to provide a method of making the surface of substrates, such as metal, ceramics, glass, plastic, fiber, paper and wood, water- and oil repellent by covering the surface of the substrates with an extremely durable ultra thin film.

It is the another object of this invention to provide water- and oil repellent materials for apparel which are durable and the body does not get sweaty in wearing clothes made of the materials for apparel.

According to a first aspect of the invention we provide a water- and oil repellent substrate comprising a chemically adsorbed polymer film as a surface layer covalently bonded to the substrate by —Si— bonds, said chemically adsorbed film containing numerous water- and oil repellent functional groups.

It is preferable in this invention that the water- and oil repellent functional groups are fluorocarbon chain groups, and the covalent bonds are siloxane bonds.

It is preferable in this invention that the substrate is made of a material selected from the group consisting of fibers, metals, ceramics, glass, plastics, papers.

It is preferable in this invention that the substrate is a fiber for apparel material.

According to a second aspect of the invention we provide a water- and oil repellent substrate treatment comprising dipping and holding a substrate comprising at least one functional group at its surface selected from the group consisting of a hydroxyl group, an imino group, and a carboxyl group in a solution prepared by dissolving a surface active material comprising a fluorocarbon and a chlorosilyl group in a non-aqueous solvent, and drying the substrate taken out of the solution in a substantially moistureless atmosphere and removing the non-aqueous solvent from the substrate.

It is preferable in this invention that the surface active material containing fluorocarbon and chlorosilyl groups is

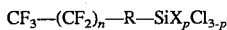
$$CF_3-(CF_2)_n-R-SiX_pCl_{3-p}$$

(where n represents 0 or an integer, R represents an alkyl group or a substituted group comprising a silicon atom or an oxygen atom or chemical bond, X represents H or a substituted group selected from the group consisting of an alkyl group and an alkoxyl group, and p represents 0, 1 or 2.).

It is preferable in this invention that the non-aqueous solvent is selected from the group consisting of a hydrocarbon-based organic solvent and a fluorocarbon-based organic solvent.

It is preferable in this invention that the active hydrogen group at the material surface is at least one functional group selected from the group consisting of a hydroxyl group, a carboxyl group, an imino group and an amino group.

It is preferable in this invention that surface functional group is a hydroxyl group provided by a plasma or corona treatment.

According to the invention, a durable, water- and oil repellent material for apparel can be provided by forming an extremely water- and oil repellent ultra thin film on the surface of the substrate via covalent bonds at a lower cost.

According to the invention, an extremely durable water- and oil repellent treatment was made easily by forming an extremely water- and oil repellent ultra thin film on the surface of the material via chemical bonds.

Subsequently, the water- and oil repellent treatment of the materials for apparel will be described with concrete examples.

A coating film of material containing at least one chlorosilyl group was formed on its surface of the substrate as follows:

by dipping and holding a material for apparel comprising a hydroxyl group, an imino group or a carboxyl group on its surface in a solution prepared by dissolving a material having a fluorocarbon group and a at least one chlorosilyl groups resolved in a non-aqueous solvent.

by drying the substrate which is taken out from the solution in an atmosphere containing substantially no moisture and removing the non-aqueous solvent remaining on the substrate. Further, when the coating film was left in air, the coating film was polymerized by a dehydrochlorination reaction between the coating film and moisture in the air. Then, the coating film was bonded to the surface of the materials for apparel via covalent bonds. Thus, an extremely water- and oil repellent ultra thin film comprising numerous fluorine groups was formed on the surface of the materials for apparel via chemical bonds.

DETAILED DESCRIPTION OF THE INVENTION

Figure 1A:
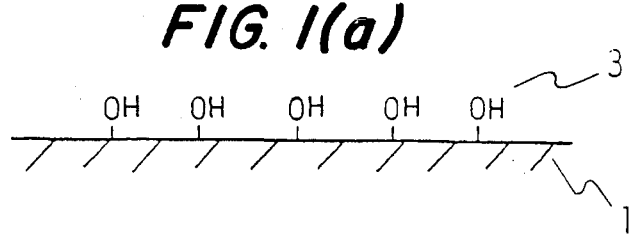
FIGS. 1 (a) to (c) show a cross section explaining the water- and oil repellent treatment of a substrate as in Example 1 and Example 3 of the invention.

According to the invention, a durable and extremely water- and oil repellent ultra thin film is formed on the surface of substrates such as glass, ceramics, fabrics, fur and cloth by a dehydrochlorination reaction between functional groups such as hydroxyl groups or imino groups on the surface of the substrate. The coating film of the material comprising a plurality of chlorosilyl groups was formed on the surface of the polymer film by dipping and holding the substrate comprising the functional groups on its surface in a solution prepared by dissolving a material comprising a fluorocarbon group and a plurality of chlorosily groups in a non-aqueous solvent and drying the substrate which is then taken out of the solution in a substantially moistureless atmosphere and removing the unreacted non-aqueous solvent remaining on the substrate. Further, when the coating film is left in an atmosphere comprising moisture, the coating film is polymerized by a dehydrochlorination reaction between the coating film and moisture in the atmosphere. The polymerized coating film contains numerous fluorine groups and reacts to moisture in the air. The substrate surface contains numerous hydroxyl groups, imino groups or carboxyl groups and thus the film is formed at the surface of the substrate through —SiO— bond or —SiN< bond.

According to the invention, a method of making the surface of the substrate water- and oil repellent comprises steps as follows:

dipping and holding a substrate, whose surface has at least one functional group such as a hydroxyl group, an imino group and a carboxyl group, in a non-aqueous solution containing a material having a fluorocarbon group and a plurality of chlorosilyl groups, drying the substrate which is taken out of the solution in a substantially moistureless or low moisture atmosphere and removing the unreacted non-aqueous solvent remaining on the substrate, removing the substrate covered by the material having a fluorocarbon group and a plurality of chlorosilyl groups in an atmosphere comprising moisture (i.e., a humid atmosphere).

In the invention, it is preferable to use

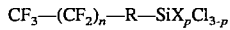

$CF_3-(CF_2)_n-R-SiX_pCl_{3-p}$ (where n represents 0 or an integer, R represents a substituted group comprising an alkyl group or a silicon atom or an oxygen atom or chemical bond) as a material having a fluorocarbon group and a plurality of chlorosilyl groups.

In the invention, it is preferable to use a hydrocarbon based solvent or a fluorocarbon based solvent as a non-aqueous solvent.

According to the invention, a durable water- and oil repellent treatment can be provided by forming an ultra thin film comprising numerous, extremely water- and oil repellent fluorines via chemical bonds. Therefore, a coating film whose surface monomolecular film comprised a plurality of chlorosilyl groups was formed by dipping and holding a substrate whose surface comprised a hydroxyl group or an imino group or a carboxyl group in a non-aqueous solution containing a material having fluorocarbon groups and a plurality of chlorosilyl groups, taking the substrate out of the solution, and removing the unreacted non-aqueous solution remaining on the substrate by drying in a substantially moistureless or low moisture atmosphere. Further, the coating film was polymerized by a dehydrochlorination reaction between the moisture in the air by exposing to an atmosphere containing moisture (i.e., humid air). Then an extremely water- and oil repellent ultra thin polymer film was formed on the surface of the substrate via chemical bonds as a dehydrochlorination reaction was also brought about between the coating film and the surface of the substrate.

$CF_3(CF_2)_7(CH_2)_2SiCl_3$, $CF_3(CF_2)_5(CH_2)_2SiCl_3$, $CF_3CH_2O(CH_2)_{15}SiCl_3$, $CF_3(CH_2)_2Si(CH_3)_2(CH_2)_{15}SiCl_3$, $F(CF_2)_4(CH_2)_2Si(CH_3)_2(CH_2)_9SiCl_3$, $CF_3COO(CH_2)_{15}SiCl_3$ are available as a material comprising a fluorocarbon group and a plurality of chlorosilyl groups.

It is preferable to use a hydrocarbon based solvent or a hydrogen fluoride based solvent as a non-aqueous solvent as they are not substantially toxic.

According to the invention, a water- and oil repellent material for apparel has an ultra thin film comprising numerous water- and oil repellent functional groups formed on the surface of the material via covalent bonds containing —Si— bonds.

According to the invention, it is preferable that a functional group of the water- and oil repellent is a fluorocarbon group and the covalent bonds are siloxane bonds.

According to the invention, a durable water- and oil repellent material for apparel can be provided by forming an ultra thin film containing numerous water- and oil repellent functional groups via covalent bonds having —Si— groups on the surface of the material. Further, as an ultra thin film at the nanometer level was formed on the surface of the material, the ultra thin film does not substantially prevent breathability and a body does not get sweaty in wearing clothes made of the substrate above mentioned.

According to a preferred embodiment of the invention, the water- and oil repellent functional group is fluorine and the covalent bond is a siloxane bond. A durable, water- and oil repellent material for apparel can be provided by forming an ultra thin film comprising numerous, extremely water- and oil repellent fluorine groups on the surface of the material via chemical bonds.

Subsequently, a detailed description of the invention will be described with concrete examples.

EXAMPLE 1

A coating film 2, being about 200 angstroms in thickness and comprising fluorocarbon groups and a plurality of chlorosilane groups, was formed as follows:

washing a processed glass substrate (any substrate such as metal, ceramics, plastic and fabrics comprising a functional group on its surface to bring about a dehydrochlorination reaction between the functional group and the chlorosilane group such as a hydroxyl group or an imino group or a carboxyl group are available) with pure water, dipping and holding the substrate in a solution prepared by dissolving 1% by weight of a chemical compound comprising fluorocarbon groups and a plurality of chlorosilane groups, e.g.,

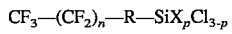

Figure 1B:
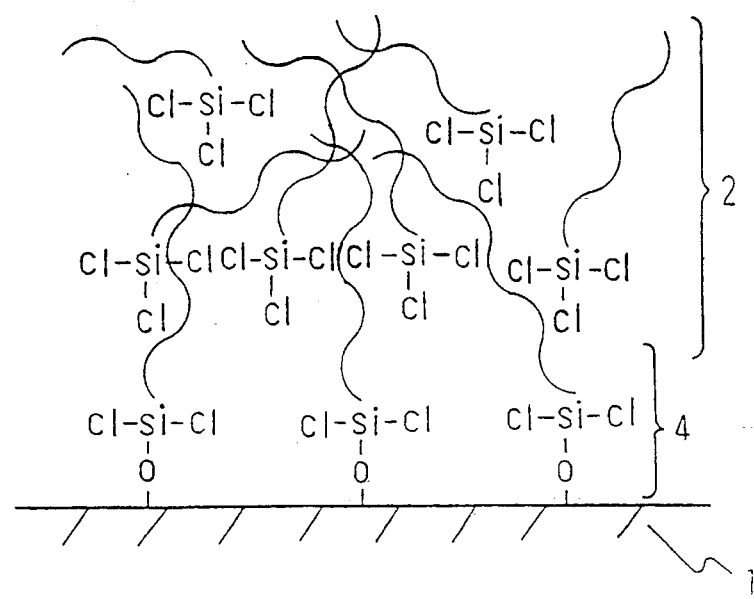
Figure 1C:
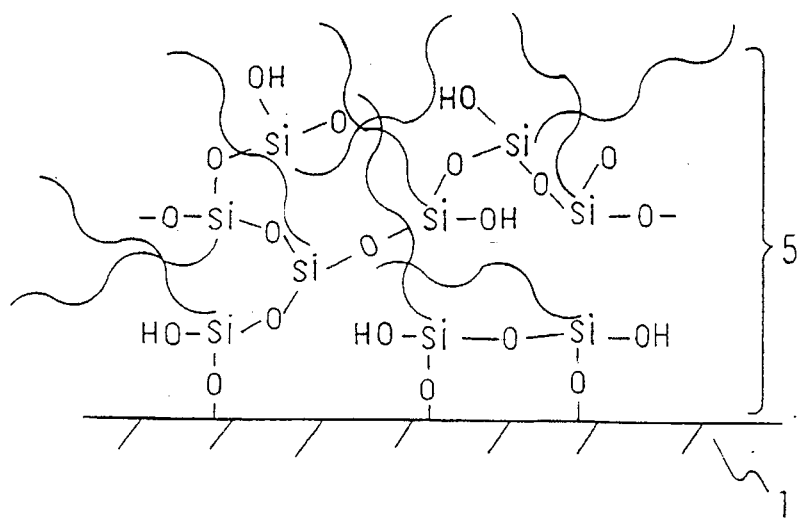

(where n represents 0 or an integer, R represents an alkyl group or a substituted group comprising a silicon atom or an oxygen atom or a chemical bond, X represents H or a substituted group such as an alkyl group or an alkoxyl group and p represents 0, 1 or 2.), e.g., $CF_3(CF_2)_7(CH_2)_7(CH_2)_2SiCl_3$, in a fluorocarbon based solvent e.g. (Afluid: Asahi glass Co.,) for about ten minutes.

drying the unreacted solvent remaining on the substrate in a substantially moistureless or low moisture atmosphere (preferably less than about 5% relative humidity) without washing with an organic solvent. When the coating film 2 was formed, a material comprising some fluorocarbon groups and a chlorosilane group was fixed on the surface of the substrate via siloxane bonds which was brought about by a dehydrochlorination reaction between the material above mentioned and a hydroxyl group 3 on the surface of the substrate (FIG. 1 (b)). Then, when the substrate was left in an atmosphere comprising moisture (i.e., a humid atmosphere of more than about 30% of relative humidity such as air), the coating film and the unreacted chlorosilyl groups of the material having the fixed fluorocarbon groups and chlorosilane groups were polymerized by a dehydrochlorination reaction between moisture in the air. The coating film contained numerous fluorine groups and it was bonded to the surface of the substrate via siloxane bonds 4. Hence, an extremely water- and oil repellent ultra thin polymerized film 5 was formed on the surface of the substrate (FIG. 1 (c)).

Further, the ultra thin polymer film was covalently bonded to the substrate via siloxane bonds, and was inseparable by scraping and washing the substrate. The wetting angle to water of the substrate was about 150°.

EXAMPLE 2

A coating film 12, being about 100 angstroms in thickness and comprising fluorocarbon groups and a plurality of chlorosilane groups, was formed as follows:

washing processed nylon-ABC resin substrate (polymer alloy or polymer blend) with pure water, dipping and holding the substrate in a solution prepared by dissolving 1% by weight of a material having fluorocarbon groups and a plurality of chlorosilyl groups e.g.

Figure 2A:
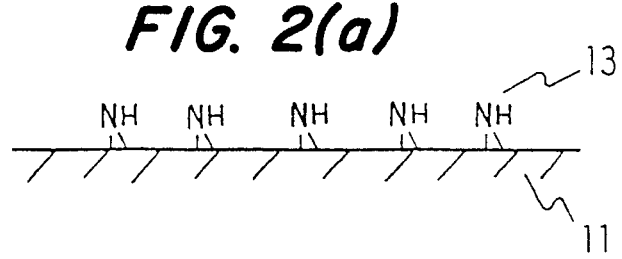
FIGS. 2 (a) to (c) show a cross section explaining the water- and oil repellent treatment of a substrate as in Example 2 and Example 4 of the invention.
Figure 2B:
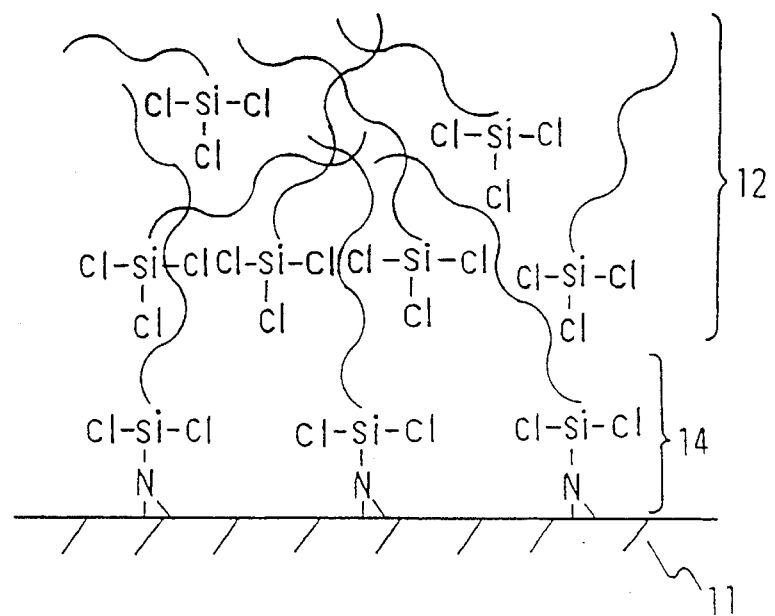
Figure 2C:
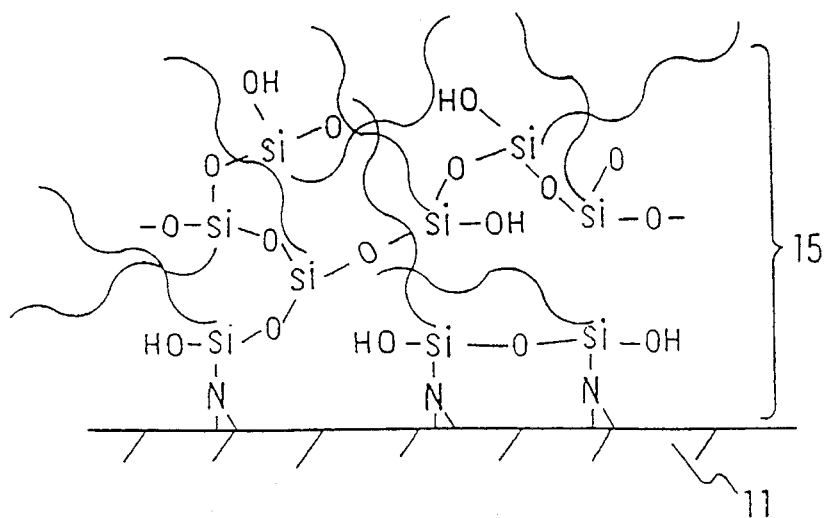

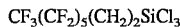

in a hydrocarbon based solvent (n-hexane) for about twenty minutes, evaporating the unreacted solvent remaining on the substrate and drying the substrate in a substantially moistureless or low moisture atmosphre (preferably less than about 5% relative humidity) without washing with an organic solvent. When the coating film 12 was formed, a material comprising some fluorocarbon groups and the chlorosilane groups was fixed on the surface of the substrate via siloxane bonds which was made by a dehydrochlorination reaction between the material above mentioned and an imino group 13 on the surface of the substrate (FIG. 2 (b)). Then, when the substrate was left in an atmosphere comprising moisture, i.e., a humid atmosphere such as air, the coating film above mentioned and the unreacted chlorosilyl groups of the material comprising the fixed fluorocarbon groups and chlorosilane groups were polymerized by a dehydrochlorination reaction with the moisture in the air. The coating film above mentioned contains numerous fluorine groups and was bonded to the surface of the substrate via —SiN< bonds. Hence, an extremely water- and oil repellent ultra thin polymerized film 15 was formed on the surface of the substrate (FIG. 2 (c)).

Further, the ultra thin film was covalently bonded to the substrate via —SiN< bonds and was inseparable by scraping and washing the substrate. The wetting angle of the substrate to water was extremely high, 130°.

In the example above mentioned, $CF_3(CF_2)_7(CH_2)_2SiCl_3$, and $CF_3(CF_2)_5(CH_2)_2SiCl_3$ were used as a material comprising a fluorocarbon group and a chlorosilane group and $CF_3CH_2O(CH_2)_{15}SiCl_3$, $CF_3(CH_2)_2Si(CH_3)_2(CH_2)_9SiCl_3$, $CF_3COO(CH_2)_{15}SiCl_3$ were also available.

In addition, the substrate whose surface was roughened about 10–0.1 μm was used in Example 1 and Example 2 and in that case, the water-repellent angle of the substrate was about 160° or 150°.

EXAMPLE 3

Processed cotton fabrics for a rain coat or any fabrics such as fur or leather comprising a functional group on its surface which brings about a dehydrochlorination reaction between a chlorosilane group such as a hydroxyl group, an imino group and a carboxyl group was washed with pure water and dipped and held in a solution prepared by dissolving a material having fluorocarbon groups and a plurality of chlorosilane groups shown as follows:

$$CF_3—(CF_2)_n—R—SiX_pCl_{3-p}$$

(where n represents 0 or an integer, R represents an alkyl group or a substituted group comprising a silicon atom or an oxygen atom or a chemical bond, X represents H or a substituted group such as an alkyl group or an alkoxyl group, and p represents 0, 1 or 2.) The material above mentioned was diluted with a non-aqueous solvent.

$CF_3(CF_2)_7(CH_2)_2SiCl_3$ was used as an example of a chemical compound as shown above. Coating film 2, being about 200 angstroms (20 nm) in thickness and comprising an unreacted fluorocarbon group and a plurality of chlorosilane groups remaining on the surface of the cotton fiber of the fabric 1 was formed as follows:

dipping and holding a cotton fabric, for about ten minutes, in a solution prepared by dissolving 1% by weight of the chemical compound above mentioned in a fluorocarbon based solvent (for example, Afluid: Asahi glass Co.,)

drying the solvent of the fabric in a substantially moistureless or low moisture atmosphere (preferably less than about 5% relative humidity) without washing with an organic solvent. When the coating film 2 was formed on the cotton fiber surface, a material comprising some fluorocarbon groups and a chlorosilane group was fixed on the surface of the cotton fiber via siloxane bonds which was brought by a dehydrochlorination reaction between the hydroxyl Groups on the surface of the cotton fiber 3 (FIG. 1 (b)). Then, when the cotton fabric above mentioned was left in an atmosphere containing moisture such as humid air (preferably more than about 30 relative humidity), an unreacted chlorosilyl group of the material comprising the coating film with the fixed fluorocarbon groups and chlorosilane groups on the surface of the cotton fiber, the film was polymerized by a dehydrochlorination reaction between moisture in the air. The coating film above mentioned contained numerous fluorine groups and was bonded to the surface of the cotton fiber via siloxane bonds 4. Thus, an extremely water- and oil repellent ultra thin polymerized film 5 was formed on the surface of the cotton fabric (FIG. 1 (c)).

When a cotton fabric was dipped and held in a solution prepared by dissolving an equal ratio of $$CF_3(CF_2)_7(CH_2)_2SiCl_3$$

and pyridine (any alkali which does not react with a chlorosilyl group and contains no moisture is available) in a fluorocarbon based solvent, a coating film was formed without deteriorating the cotton fabric. By adding a great deal of pyridine, hydrochloric acid which was formed during the reaction was neutralized. Thus, the cotton fabric was not deteriorated.

The ultra thin film above mentioned comprising a fluorocarbon group was covalently bonded to the cotton fiber via siloxane bonds, and was inseparable by scraping and washing the substrate. The wetting angle to water of water- and oil repellent cotton fabric substrate was about 170°.

EXAMPLE 4

A coating film 12, being about 100 angstroms (10 nm) in thickness and comprising fluorocarbon groups and a plurality of chlorosilyl groups was formed as follows:

washing processed nylon fabric with pure water, dipping and holding the nylon fabric in a solution, for about twenty minutes, prepared by dissolving 1% by weight of a material comprising fluorocarbon groups and a plurality of chlorosilyl groups such as $CF_3(CF_2)_5(CH_2)_2SiCl_3$ in a hydrocarbon based solvent (normal hexane).

drying the substrate in a substantially moistureless or low moisture atmosphere (preferably less than about 5% relative humidity) without washing with an organic solvent. When the coating film 12 was formed, a material comprising some fluorocarbon groups and a chlorosilyl group was fixed on the surface of the nylon fiber via siloxane bonds (—SiO—) 14 which was brought about by a dehydrochlorination reaction between an imino group on the surface of the nylon fiber (FIG. 2 (b)). Then, when the fabric was left in an atmosphere comprising moisture such as humid air (more than about 30% relative humidity), unreacted chlorosilyl groups of the material comprising the coating film, the fixed the fluorocarbon groups and the chlorosilane groups was polymerized by a dehydrochlorination reaction between moisture in the air. The coating film above mentioned contained numerous fluorocarbon groups and was bonded to the fiber of the substrate via —SiN< bonds. Hence, an extremely water- and oil repellent ultra thin polymerized film 15 was formed on the surface of the nylon fiber (FIG. 2 (c)).

Further, the ultra thin film was covalently bonded to a nylon fiber via —SiN< bonds, and was inseparable by scraping and washing the substrate. The wetting angle to water of nylon cloth which was made of nylon fabrics was extremely high, about 170°.

In the example of the invention, $$CF_3(CF_2)_7(CH_2)_2SiCl_3,$$

$$CF_3(CF_2)_5(CH_2)_2SiCl_3$$

was used as a material comprising a fluorocarbon group and a chlorosilane group. However, material shown as follows were also available.

$$CF_3CH_2O(CH_2)_{15}SiCl_3,$$

$$CF_3(CH_2)_2Si(CH_3)_2(CH_2)_{15}SiCl_3,$$

$$F(CF_2)_4(CH_2)_2Si(CH_3)_2(CH_2)_9SiCl_3,$$

$$CF_3COO(CH_2)_{15}SiCl_3$$

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim:

1. A water- and oil repellent substrate comprising a chemically adsorbed non-oriented polymer film as a surface layer covalently bonded to the substrate by siloxane bonds, said chemically adsorbed film containing water- and oil repellent functional groups, wherein said water- and oil repellent functional groups are fluorine groups, the substrate is a fiber for apparel, and the wetting angle of the substrate to water is 130° or more.

* * * * *